United States Patent
Gourlaouen et al.

(10) Patent No.: US 7,261,744 B2
(45) Date of Patent: Aug. 28, 2007

(54) METHOD FOR DYEING OR COLORING HUMAN KERATIN MATERIALS WITH LIGHTENING EFFECT USING A COMPOSITION COMPRISING AT LEAST ONE FLUORESCENT COMPOUND AND AT LEAST ONE OPTICAL BRIGHTENER

(75) Inventors: Luc Gourlaouen, Asnieres (FR); Florent Pastore, Rueil Malmaison (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 10/742,995

(22) Filed: Dec. 23, 2003

(65) Prior Publication Data

US 2006/0010617 A1    Jan. 19, 2006

Related U.S. Application Data

(60) Provisional application No. 60/435,868, filed on Dec. 24, 2002.

(30) Foreign Application Priority Data

Dec. 24, 2002   (FR)   .................................. 02 16669

(51) Int. Cl.
*A61K 7/13*   (2006.01)
(52) U.S. Cl. ....................... 8/405; 8/406; 8/407; 8/410; 8/411; 8/421; 8/637.1; 8/645; 8/648
(58) Field of Classification Search ................... 8/405, 8/406, 407, 410, 411, 421, 637.1, 645, 648
See application file for complete search history.

(56) References Cited

U.S. PATENT DOCUMENTS 2,261,002 A   10/1941   Ritter
2,271,378 A   1/1942    Searle
2,273,780 A   2/1942    Ditmar (Continued)

FOREIGN PATENT DOCUMENTS

AT   302 534   10/1972

(Continued)

OTHER PUBLICATIONS

French Search Report for FR 0 216 669, dated Aug. 6, 2003.

(Continued)

*Primary Examiner*—Eisa Elhilo
(74) *Attorney, Agent, or Firm*—Finnegan, Henderson, Farabow, Garrett & Dunner, LLP

(57) ABSTRACT

Disclosed herein are a method of dyeing or coloring, with a lightening effect, a human keratin material comprising applying a composition comprising, in a cosmetically acceptable medium, at least one fluorescent compound and at least one optical brightener; a composition comprising, in a cosmetically acceptable medium, at least one fluorescent compound and at least one optical brightener which are both soluble in the medium; and a device using such a composition comprising at least two compartments, wherein at least one comprises, in a cosmetically acceptable medium, a composition comprising at least one fluorescent compound and at least one optical brightener and optionally at least one additional ingredient chosen from direct dyes, oxidation bases and couplers, and at least one other compartment comprises a composition comprising at least one oxidizing agent.

80 Claims, 1 Drawing Sheet

U.S. PATENT DOCUMENTS

| | | |
|---|---|---|
| 2,375,853 A | 5/1945 | Kirby et al. |
| 2,388,614 A | 11/1945 | Kirby et al. |
| 2,454,547 A | 11/1948 | Bock et al. |
| 2,798,053 A | 7/1957 | Brown |
| 2,851,424 A | 9/1958 | Switzer et al. ........... 252/301.2 |
| 2,923,692 A | 2/1960 | Ackerman et al. |
| 2,961,347 A | 11/1960 | Floyd |
| 2,979,465 A | 4/1961 | Parran et al. |
| 3,014,041 A | 12/1961 | Hausermann et al. |
| 3,206,462 A | 9/1965 | McCarty |
| 3,227,615 A | 1/1966 | Korden |
| 3,472,840 A | 10/1969 | Stone et al. |
| 3,632,559 A | 1/1972 | Matter et al. |
| 3,639,127 A | 2/1972 | Brooker et al. |
| 3,658,985 A | 4/1972 | Olson, Jr. et al. |
| 3,856,550 A | 12/1974 | Bens et al. ................ 117/33.5 |
| 3,874,870 A | 4/1975 | Green et al. |
| 3,910,862 A | 10/1975 | Barabas et al. |
| 3,912,808 A | 10/1975 | Sokol |
| 3,915,921 A | 10/1975 | Schlatzer, Jr. |
| 3,917,817 A | 11/1975 | Vanlerberghe et al. |
| 3,929,990 A | 12/1975 | Green et al. |
| 3,966,904 A | 6/1976 | Green et al. |
| 3,986,825 A | 10/1976 | Sokol |
| 4,001,432 A | 1/1977 | Green et al. |
| 4,005,193 A | 1/1977 | Green et al. |
| 4,013,787 A | 3/1977 | Varlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,075,136 A | 2/1978 | Schaper |
| 4,131,576 A | 12/1978 | Iovine et al. |
| 4,157,388 A | 6/1979 | Christiansen |
| 4,165,367 A | 8/1979 | Chakrabarti |
| 4,166,894 A | 9/1979 | Schaper |
| 4,172,887 A | 10/1979 | Vanlerberghe et al. |
| 4,185,087 A | 1/1980 | Morlino |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,223,009 A | 9/1980 | Chakrabarti |
| 4,237,243 A | 12/1980 | Quack et al. |
| 4,240,450 A | 12/1980 | Grollier et al. |
| 4,256,458 A | 3/1981 | Degen et al. |
| 4,277,581 A | 7/1981 | Vanlerberghe et al. |
| 4,381,919 A | 5/1983 | Jacquet et al. |
| 4,422,853 A | 12/1983 | Jacquet et al. |
| 4,445,521 A | 5/1984 | Grollier et al. |
| 4,509,949 A | 4/1985 | Huang et al. |
| 4,517,174 A | 5/1985 | Jacquet et al. |
| 4,591,610 A | 5/1986 | Grollier |
| 4,608,250 A | 8/1986 | Jacquet et al. |
| 4,693,935 A | 9/1987 | Mazurek |
| 4,702,906 A | 10/1987 | Jacquet et al. |
| 4,719,099 A | 1/1988 | Grollier et al. |
| 4,719,282 A | 1/1988 | Nadolsky et al. |
| 4,728,571 A | 3/1988 | Clemens et al. |
| 4,761,273 A | 8/1988 | Grollier et al. |
| 4,781,724 A | 11/1988 | Wajaroff et al. |
| 4,823,985 A | 4/1989 | Grollier et al. ................ 222/1 |
| 4,839,166 A | 6/1989 | Grollier et al. |
| 4,948,579 A | 8/1990 | Jacquet et al. |
| 4,961,925 A | 10/1990 | Tsujino et al. |
| 4,972,037 A | 11/1990 | Garbe et al. |
| 4,996,059 A | 2/1991 | Grollier et al. |
| 5,009,880 A | 4/1991 | Grollier et al. |
| 5,057,311 A | 10/1991 | Kamegai et al. |
| 5,089,252 A | 2/1992 | Grollier et al. |
| 5,139,037 A | 8/1992 | Grollier et al. |
| 5,188,639 A | 2/1993 | Schultz et al. |
| 5,196,189 A | 3/1993 | Jacquet et al. |
| 5,275,808 A | 1/1994 | De Groot et al. |
| 5,316,551 A | 5/1994 | Wenke |
| 5,356,438 A | 10/1994 | Kim et al. |
| 5,445,655 A | 8/1995 | Kuhn et al. |
| 5,635,461 A | 6/1997 | Onitsuka et al. |
| 5,708,151 A | 1/1998 | Möckli ........................ 534/608 |
| 5,733,343 A | 3/1998 | Mockli |
| 5,744,127 A * | 4/1998 | Giuseppe et al. .............. 424/59 |
| 5,792,221 A | 8/1998 | Lagrange et al. |
| 5,830,446 A | 11/1998 | Berthiaume et al. ........ 424/70.1 |
| 5,833,997 A | 11/1998 | Mahieu et al. |
| 5,853,708 A | 12/1998 | Cauwet et al. |
| 5,873,494 A | 2/1999 | Dallas, Jr. |
| 5,958,392 A | 9/1999 | Grollier et al. |
| 5,961,667 A | 10/1999 | Doehling et al. |
| 5,962,522 A | 10/1999 | Wacher et al. |
| 6,001,135 A | 12/1999 | Rondeau et al. |
| 6,106,577 A * | 8/2000 | Audousset et al. ............. 8/403 |
| 6,120,780 A | 9/2000 | Dupuis et al. |
| 6,156,077 A | 12/2000 | Shibata et al. |
| 6,180,666 B1 | 1/2001 | Wacher et al. |
| 6,260,556 B1 | 7/2001 | Legrand et al. |
| 6,375,958 B1 | 4/2002 | Cauwet et al. |
| 6,391,062 B1* | 5/2002 | Vandenbossche et al. ...... 8/405 |
| 6,436,151 B2 | 8/2002 | Cottard et al. |
| 6,436,153 B2 | 8/2002 | Rondeau |
| 6,475,248 B2 | 11/2002 | Ohashi et al. |
| 6,570,019 B2 | 5/2003 | Pasquier et al. |
| 6,576,024 B1 | 6/2003 | Lang et al. |
| 6,592,630 B2 | 7/2003 | Matsunaga et al. |
| 6,616,709 B2 | 9/2003 | Ohashi et al. |
| 6,712,861 B2 | 3/2004 | Rondeau |
| 2001/0010812 A1 | 8/2001 | Chevalier et al. |
| 2001/0023514 A1 | 9/2001 | Cottard et al. |
| 2001/0023515 A1 | 9/2001 | Cottard et al. |
| 2001/0031270 A1 | 10/2001 | Douin et al. |
| 2001/0034914 A1 | 11/2001 | Saunier et al. |
| 2001/0054206 A1* | 12/2001 | Matsunaga et al. ............. 8/405 |
| 2001/0055580 A1 | 12/2001 | Belli et al. |
| 2002/0004956 A1 | 1/2002 | Rondeau |
| 2002/0012681 A1 | 1/2002 | George et al. |
| 2002/0026676 A1 | 3/2002 | Ohashi et al. |
| 2002/0034489 A1* | 3/2002 | Wiegland et al. ......... 424/70.24 |
| 2002/0046431 A1 | 4/2002 | Laurent et al. |
| 2002/0046432 A1 | 4/2002 | Rondeau |
| 2002/0088063 A1 | 7/2002 | Ohashi et al. |
| 2002/0131941 A1 | 9/2002 | Habeck et al. |
| 2002/0176836 A9 | 11/2002 | Belli et al. |
| 2002/0176875 A9 | 11/2002 | Douin et al. |
| 2003/0000023 A9 | 1/2003 | Rondeau |
| 2003/0019052 A1 | 1/2003 | Pratt |
| 2003/0019053 A9 | 1/2003 | Rondeau |
| 2003/0055268 A1 | 3/2003 | Pasquier et al. ............ 548/453 |
| 2003/0074747 A1 | 4/2003 | Vuarier et al. |
| 2003/0124079 A1 | 7/2003 | Mougin et al. |
| 2003/0131424 A1 | 7/2003 | Audousset et al. |
| 2004/0019981 A1 | 2/2004 | Cottard et al. |
| 2004/0034945 A1 | 2/2004 | Javet et al. |
| 2004/0037796 A1 | 2/2004 | Cottard et al. |
| 2004/0049860 A1 | 3/2004 | Cottard et al. |
| 2004/0105830 A1 | 6/2004 | Bloswell et al. |
| 2004/0141943 A1 | 7/2004 | Mougin et al. |
| 2004/0148711 A1 | 8/2004 | Rondeau |
| 2004/0205901 A1 | 10/2004 | Cottard et al. |
| 2004/0258641 A1 | 12/2004 | Plos et al. |
| 2005/0005368 A1 | 1/2005 | Plos et al. |
| 2005/0005369 A1 | 1/2005 | Plos et al. |
| 2005/0008593 A1 | 1/2005 | Plos et al. |
| 2005/0028301 A1 | 2/2005 | Pastore |

| | | | | | | |
|---|---|---|---|---|---|---|
| 2005/0144741 A1 | 7/2005 | Lang et al. | | GB | 759385 | 10/1956 |
| | | | | GB | 1214394 | 1/1970 |
| FOREIGN PATENT DOCUMENTS | | | | GB | 1546809 | 5/1979 |
| | | | | GB | 1554331 | 10/1979 |
| CA | 1255603 | 6/1989 | | JP | 48-17362 | 5/1973 |
| CH | 487 231 | 3/1970 | | JP | 54-86521 | 7/1979 |
| DE | 33 13 332 | 10/1984 | | JP | 2-200612 | 8/1990 |
| DE | 196 46 804 | 5/1997 | | JP | 6-128128 | 5/1994 |
| DE | 199 23 438 A1 | 11/2000 | | JP | 6-183935 | 7/1994 |
| DE | 199 26 377 A1 | 12/2000 | | JP | 6-227954 | 8/1994 |
| DE | 100 29 441 | 1/2002 | | JP | 8-183716 | 7/1996 |
| DE | 101 41 683 A1 | 6/2003 | | JP | 8-208448 | 8/1996 |
| DE | 101 48 844 A1 | 10/2003 | | JP | 8-259426 | 10/1996 |
| EP | 0 087 060 B1 | 8/1983 | | JP | 9-183714 | 7/1997 |
| EP | 0 095 238 A2 | 11/1983 | | JP | 10-23629 | 9/1998 |
| EP | 0 080 976 B1 | 9/1986 | | JP | 11-021214 | 1/1999 |
| EP | 0 173 109 | 10/1989 | | JP | 11-60453 | 3/1999 |
| EP | 0 370 470 | 5/1990 | | JP | 11-343218 | 12/1999 |
| EP | 0 412 704 B1 | 2/1991 | | JP | 2000-01417 | 1/2000 |
| EP | 0 412 707 B1 | 2/1991 | | JP | 2000-86472 | 3/2000 |
| EP | 0 445 342 B1 | 9/1991 | | JP | 2000-505841 | 5/2000 |
| EP | 0 486 135 B1 | 5/1992 | | JP | 2001-172120 | 6/2001 |
| EP | 0 122 324 B2 | 2/1993 | | JP | 2001-220330 | 8/2001 |
| EP | 0 337 354 B1 | 2/1994 | | JP | 2001-226217 | 8/2001 |
| EP | 0 582 152 B1 | 2/1994 | | JP | 2001-261534 | 9/2001 |
| EP | 0 395 282 | 3/1995 | | JP | 2001-261536 | 9/2001 |
| EP | 0 503 853 | 5/1996 | | JP | 2001 294519 | 10/2001 |
| EP | 0 714 954 | 6/1996 | | JP | 2001-302473 | 10/2001 |
| EP | 0 733 355 A2 | 9/1996 | | JP | 2001-516701 | 10/2001 |
| EP | 0 808 150 | 11/1997 | | JP | 2001-516705 | 10/2001 |
| EP | 0 815 828 B1 | 6/1999 | | JP | 2001-516706 | 10/2001 |
| EP | 0 970 684 A1 | 1/2000 | | JP | 2001-516707 | 10/2001 |
| EP | 1 023 891 B1 | 8/2000 | | JP | 2002-12523 | 1/2002 |
| EP | 1 142 559 | 4/2001 | | JP | 2002-12530 | 1/2002 |
| EP | 1 099 437 | 5/2001 | | JP | 2002-47151 | 2/2002 |
| EP | 1 132 076 A1 | 9/2001 | | JP | 2002-226338 | 8/2002 |
| EP | 1 133 977 A2 | 9/2001 | | JP | 2002-249419 | 9/2002 |
| EP | 1 191 041 A2 | 3/2002 | | JP | 2002-326911 | 11/2002 |
| FR | 1492597 | 9/1966 | | JP | 2003-55177 | 2/2003 |
| FR | 1583363 | 10/1969 | | JP | 2004-059468 | 2/2004 |
| FR | 2077143 | 10/1971 | | JP | 2004-307494 | 11/2004 |
| FR | 2080759 | 11/1971 | | JP | 2004-307495 | 11/2004 |
| FR | 2103210 | 7/1972 | | WO | WO93/11103 | 6/1993 |
| FR | 2162025 | 7/1973 | | WO | WO93/23009 | 11/1993 |
| FR | 2190406 | 2/1974 | | WO | WO93/23446 | 11/1993 |
| FR | 2252840 | 6/1975 | | WO | WO94/02022 | 2/1994 |
| FR | 2270846 | 12/1975 | | WO | WO95/00578 | 1/1995 |
| FR | 2280361 | 2/1976 | | WO | WO95/01772 | 1/1995 |
| FR | 2316271 | 1/1977 | | WO | WO95/15144 | 6/1995 |
| FR | 2320330 | 3/1977 | | WO | WO97/18795 | 5/1997 |
| FR | 2336434 | 7/1977 | | WO | WO99/12846 | 3/1999 |
| FR | 2368508 | 5/1978 | | WO | WO99/13822 | 3/1999 |
| FR | 2383660 | 10/1978 | | WO | WO99/13823 | 3/1999 |
| FR | 2393573 | 1/1979 | | WO | WO99/13824 | 3/1999 |
| FR | 2411219 | 7/1979 | | WO | WO99/13828 | 3/1999 |
| FR | 2416723 | 9/1979 | | WO | WO99/13841 | 3/1999 |
| FR | 2470596 | 6/1981 | | WO | WO99/13844 | 3/1999 |
| FR | 2505348 | 11/1982 | | WO | WO99/13845 | 3/1999 |
| FR | 2519863 | 7/1983 | | WO | WO99/13846 | 3/1999 |
| FR | 2542997 | 9/1984 | | WO | WO99/13847 | 3/1999 |
| FR | 2 586 913 | 3/1987 | | WO | WO99/13849 | 3/1999 |
| FR | 2589476 | 5/1987 | | WO | WO99/20235 A1 | 4/1999 |
| FR | 2598611 | 11/1987 | | WO | WO99/36045 | 7/1999 |
| FR | 2 692 572 | 12/1993 | | WO | WO 00/68282 | 11/2000 |
| FR | 2741261 | 5/1997 | | WO | WO 00/71085 A2 | 11/2000 |
| FR | 2 773 470 | 7/1999 | | WO | WO 01/43714 A1 | 6/2001 |
| FR | 2 773 864 | 7/1999 | | WO | WO 01/62759 | 8/2001 |
| FR | 2 797 877 | 3/2001 | | WO | WO 01/78669 | 10/2001 |
| FR | 2800612 | 5/2001 | | WO | WO 02/32386 A2 | 4/2002 |
| FR | 2811993 | 1/2002 | | WO | WO 02/38115 A1 | 5/2002 |
| FR | 2820032 | 8/2002 | | WO | WO 02/39964 A1 | 5/2002 |
| FR | 2830189 | 4/2003 | | WO | WO 02/45673 A2 | 6/2002 |
| GB | 746 864 | 3/1956 | | WO | WO 02/058646 A1 | 8/2002 |

| WO | WO 02/058647 A1 | 8/2002 |
| WO | WO 02/074270 | 9/2002 |
| WO | WO 03/022232 A2 | 3/2003 |
| WO | WO 03/028685 A1 | 4/2003 |
| WO | WO 03/029359 | 4/2003 |

OTHER PUBLICATIONS

Zviak, Charles; Sciences des traitements capillaires, pp. 215, 278 (1988).
English language abstract from esp@cenet for EP 1 099 437, published May 16, 2001.
English language Derwent Abstract for DE 33 13 332, published Oct. 18, 1984.
English language Derwent Abstract for DE 100 29 441, published Jan. 3, 2002.
English language abstract from esp@cenet for FR 2 692 572, published Dec. 24, 1993.
English language Derwent Abstract for FR 2 773 864, published Jul. 16, 1999.
English language abstract from esp@cenet for FR 2 797 877, published Mar. 2, 2001.
English language Derwent Abstract for JP 2001 294519, published Oct. 23, 2001.
CAS Abstract for JP 2000-136340—Chemical Abstracts Service; Database Accession No. 2000: 317079; XP-002269220, JP 2000136340 (Pentel Co., Ltd.), May 16, 2000.
Co-pending U.S. Appl. No. 10/814,334, filed Apr. 1, 2004.
Co-pending U.S. Appl. No. 10/814,333, filed Apr. 1, 2004.
Co-pending U.S. Appl. No. 10/814,430, filed Apr. 1, 2004.
Co-pending U.S. Appl. No. 10/814,305, filed Apr. 1, 2004.
Co-pending U.S. Appl. No. 10/814,300, filed Apr. 1, 2004.
Co-pending U.S. Appl. No. 10/814,335, filed Apr. 1, 2004.
Co-pending U.S. Appl. No. 10/814,428, filed Apr. 1, 2004.
Co-pending U.S. Appl. No. 10/490,869, filed Apr. 1, 2004.
Co-pending U.S. Appl. No. 10/814,236, filed Apr. 1, 2004.
Co-pending U.S. Appl. No. 10/814,338, filed Apr. 1, 2004.
Co-pending U.S. Appl. No. 10/814,585, filed Apr. 1, 2004.
Co-pending U.S. Appl. No. 10/814,336, filed Apr. 1, 2004.
English Language Derwent Abstract of DE 101 41 683.
English Language Derwent Abstract of DE 101 48 844.
English Language Derwent Abstract of DE 199 23 438.
English Language Derwent Abstract of DE 199 26 377.
English Language Derwent Abstract of EP 0 080 976.
English Language Derwent Abstract of EP 0 087 060.
English Language Derwent Abstract of EP 1 023 891.
English Language Derwent Abstract of FR 2,800,612.
English Language Abstract of FR 2 598 476 (EP 0 225 261) from EPO website.
English Language Derwent Abstract of JP 10-23629.
English Language Derwent Abstract of JP 11-060453.
English Language Derwent Abstract of JP 11-21214.
English Language Derwent Abstract of JP 2000-1417.
English Language Derwent Abstract of JP 2000-086472.
English Language Derwent Abstract of JP 2001-172120.
English Language Derwent Abstract of JP 2001-261534.
English Language Derwent Abstract of JP 2001-516701.
English Language Derwent Abstract of JP 2001-516706.
English Language Derwent Abstract of JP 2001-516707.
English Language Derwent Abstract of JP 2002-226338.
English Language Abstract of JP 2002-249419 from Japio database.
English Language Derwent Abstract of JP 2004-59468.
English Language Derwent Abstract of JP 2-200612.
English Language Derwent Abstract of JP 6-183935.
English Language Derwent Abstract of JP 6-226954.
English Language Derwent Abstract of JP 8-183716.
English Language Derwent Abstract of JP 8-208448.
French Search Report for French Patent Application No. FR 03/04021, priority document for U.S. Appl. No. 10/814,337, filed Dec. 8, 2003, Examiner A. Lindner.
French Search Report for French Patent Application No. FR 03/04022, priority document for co-pending U.S. Appl. No. 10/814,336, filed Nov. 20, 2003, Examiner A. Lindner.
French Search Report for French Patent Application No. FR 03/04024, priority document for co-pending U.S. Appl. No. 10/814,585, filed Dec. 8, 2003, Examiner A. Lindner.
French Search Report for French Patent Application No. FR 03/04026, priority document for co-pending U.S. Appl. No. 10/814,335, filed Nov. 21, 2003, Examiner T. Saunders.
French Search Report for French Patent Application No. FR 03/04027, priority document for co-pending U.S. Appl. No. 10/814,428, filed Nov. 28, 2003, Examiner A. Lindner.
French Search Report for French Patent Application No. FR 03/04028, priority document for co-pending U.S. Appl. No. 10/814,236, filed Nov. 25, 2003, Examiner T. Saunders.
French Search Report for French Patent Application No. FR 03/04029, priority document for co-pending U.S. Appl. No. 10/814,430, filed Feb. 5, 2004, Examiner D. Krische.
French Search Report for French Patent Application No. FR 03/04030, priority document for co-pending U.S. Appl. No. 10/814,300, filed Nov. 27, 2003, Examiner A. Lindner.
French Search Report for French Patent Application No. FR 03/04031, priority document for co-pending U.S. Appl. No. 10/814,333, filed Jan. 8, 2004, Examiner A. Lindner.
French Search Report for French Patent Application No. FR 03/04033, priority document for co-pending U.S. Appl. No. 10/814,334, filed Nov. 28, 2003, Examiner A. Lindner.
French Search Report for French Patent Application No. FR 03/04034, priority document for co-pending U.S. Appl. No. 10/814,338, filed Feb. 17, 2004, Examiner J-F. Glikman.
French Search Report for French Patent Application No. FR 03/04035, priority document for co-pending U.S. Appl. No. 10/814,305, filed Feb. 5, 2004, Examiner D. Krische.
International Search Report for PCT Application No. PCT/FR 02/03252, (for co-pending U.S. Appl. No. 10/490,869), filed Jan. 20, 2003, Examiner J. F. Glikman.
Office Action dated Mar. 27, 2006 in co-pending U.S. Appl. No. 10/814,334, Examiner E. Elhilo.
Office Action dated Mar. 15, 2006 in co-pending U.S. Appl. No. 10/814,337, Examiner E. Elhilo.
Office Action mailed Nov. 17, 2005 in co-pending U.S. Appl. No. 10/814,336, Examiner E. Elhilo.
Office Action mailed Nov. 3, 2005 in co-pending U.S. Appl. No. 10/490,869, Examiner E. Elhilo.
Office Action mailed Nov. 2, 2005 in co-pending U.S. Appl. No. 10/814,338, Examiner E. Elhilo.
Jacobi, Otto and Jacobi, Gertrud, "Investigation into the reciprocal action of cosmetics and the biosphere of the stratum corneuum of the skin," Cosmetics and Toiletries, 91:25-32 (Jan. 1976).
Science Des Traitements Capillaires [Hair Treatment Sciences] by Charles Zviak, 1988, published by Masson, pp. 215 and 278.
M. Schlossmann, "The Chemistry and Manufacture of Cosmetics Formulating," 2(3):522-526 (2000).
C. D. Williams et al., "Chemistry and Technology of the Cosmetics and Toiletries Industry," ed. 2, pp. 77-78 (1996).
Yuuki Kagobutsu Jilen (Dictionary of Organic Compounds), Kodansha Ltd., Aug. 10, 2002, p. 908.
G. Fonnum, J. Bakke and Fk. Hansen—Colloid Polym. Sci 271, 380-389 (1993).
Co-pending Application No. 10/814,337, filed Apr. 1, 2004.
English language Derwent Abstract of JP 2001-302473.
English language Derwent Abstract of JP 2002-326911.
English language Derwent Abstract of JP 9-183714.
English language Derwent Abstract of FR 2 773 470.
English language Derwent Abstract of WO 02/32386.
French Search Report for French Patent Application No. FR 02/16669, priority document for co-pending U.S. Appl. No. 10/742,995, filed Aug. 6, 2003, Examiner S. Grillenberger.
Mishra, J.K. et al. "Synthesis of some bischromophoric dyes containing nonabsorbing flexible bridge," Indian Journal of Chemistry, vol. 31B, pp. 118-112, Feb. 1992.
Office Action mailed Aug. 24, 2006 in co-pending U.S. Appl. No. 10/814,305, Examiner E. Elhilo.
Office Action mailed Aug. 28, 2006 in co-pending U.S. Appl. No. 10/814,236, Examiner E. Elhilo.

Office Action mailed Aug. 28, 2006 in co-pending U.S. Appl. No. 10/814,300, Examiner E. Elhilo.
Office Action mailed Jul. 7, 2006, in co-pending U.S. Appl. No. 10/814,585, Examiner E. Elhilo.
Office Action mailed Jun. 21, 2006, in co-pending U.S. Appl. No. 10/814,336, Examiner E. Elhilo.
Office Action mailed Jun. 8, 2006, in co-pending U.S. Appl. No. 10/814,430, Examiner E. Elhilo.
Office Action mailed Mar. 15, 2006 in co-pending U.S. Appl. No. 10/814,305, Examiner E. Elhilo.
Office Action mailed Mar. 23, 2006 in co-pending U.S. Appl. No. 10/814,300, Examiner E. Elhilo.
Office Action mailed Mar. 24, 2006, in co-pending U.S. Appl. No. 10/814,236, Examiner E. Elhilo.
Office Action mailed May 18, 2006, in co-pending U.S. Appl. No. 10/814,333, Examiner E. Elhilo.
Office Action mailed May 25, 2006, in co-pending U.S. Appl. No. 10/814,335, Examiner E. Elhilo.
Office Action mailed May 26, 2006, in co-pending U.S. Appl. No. 10/490,869, Examiner E. Elhilo.
Office Action mailed May 30, 2006, in co-pending U.S. Appl. No. 10/814,338, Examiner E. Elhilo.
Zviak, C., The Science of Hair Care, pp. 215 and 278 (1986).

* cited by examiner

METHOD FOR DYEING OR COLORING HUMAN KERATIN MATERIALS WITH LIGHTENING EFFECT USING A COMPOSITION COMPRISING AT LEAST ONE FLUORESCENT COMPOUND AND AT LEAST ONE OPTICAL BRIGHTENER

This application claims benefit of U.S. Provisional Application No. 60/435,868, filed Dec. 24, 2002.

Disclosed herein is a method of dyeing or coloring a human keratin material comprising applying to the keratin material a composition comprising, in a cosmetically acceptable medium, at least one fluorescent compound and at least one optical brightener. Further disclosed herein is a composition comprising, in a cosmetically acceptable medium, at least one fluorescent compound and at least one optical brightener, both of which are soluble in the medium, as well as a device comprising at least two compartments, wherein at least one compartment comprises at least one fluorescent compound and at least one optical brightener and at least one other compartment comprises at least one oxidizing agent.

It is frequently the case that individuals having colored or even dark skin may wish to lighten their skin, and for that purpose, use cosmetic or dermatological compositions which contain bleaching agents.

The substances most commonly used as bleaching agents are hydroquinone and its derivatives, kojic acid and its derivatives, azelaic acid, and arbutin and its derivatives, alone or in combination with other actives.

These agents, however, are not without their drawbacks. For example, it may be necessary to use them for prolonged periods and in large amounts in order to obtain a skin bleaching effect. Moreover, an immediate effect on applying compositions comprising them may not be observed.

Hydroquinone and its derivatives are known for their melanocyte toxicity.

In addition, kojic acid and its derivatives can have the drawback of being expensive and of hence being unsuitable for use in large amounts in products for broad commercial distribution.

There remains, therefore, a need for cosmetic compositions that can allow a lighter complexion to be obtained that may be uniform, homogeneous, and natural in appearance.

In the haircare field, in order to obtain a lighter coloring, it is conventional to employ a chemical bleaching process. This process comprises bleaching the melanins in these fibers using an oxidizing system composed in general of hydrogen peroxide alone or in combination with persalts. This operation may be carried out in the presence or absence of direct dyes and/or of oxidation dyes.

This bleaching system may have the disadvantage of degrading the keratin fibers and adversely affecting their cosmetic properties. For example, the hair may tend to become rough, more difficult to disentangle, and weaker.

It is therefore desirable to be able to have compositions that can allow the hair and other human keratin fibers to be lightened and at the same time colored, aesthetically, without degrading these fibers.

Disclosed herein are thus a method and a composition that allow a human keratin material to be dyed or colored without giving rise to at least one of the difficulties mentioned above.

Accordingly, disclosed herein is a method of dyeing or coloring a human keratin material with a lightening effect, comprising applying to the keratin material a composition comprising, in a cosmetically acceptable medium, at least one fluorescent compound and at least one optical brightener.

Further disclosed herein is a composition comprising, in a cosmetically acceptable medium, at least one fluorescent compound soluble in the medium and at least one optical brightener soluble in the medium.

Further disclosed herein is a device comprising at least two compartments, wherein at least one compartment comprises, in a cosmetically acceptable medium, a composition comprising at least one fluorescent compound and at least one optical brightener and optionally at least one additional ingredient chosen from direct dyes, oxidation bases, and couplers, and at least one other compartment comprises a composition comprising at least one oxidizing agent.

The composition and method disclosed herein may allow the human keratin materials to be dyed or colored and at the same time lightened without detriment to them.

For example, the method disclosed herein may allow a coloration or shade to be obtained for which the reflectance of the keratin materials treated in accordance with the disclosure, measured in a range of from 550 nm to 700 nm, is greater than the reflectance of the untreated materials.

The presently disclosed composition and method may also allow a coloration or shade to be obtained which is lighter than the natural coloring or shade, with a highly satisfactory aesthetic effect.

Furthermore, the existence has been observed of an interaction between the fluorescent compound and the optical brightener in the composition, which may enhance the lightening phenomenon and broaden the range within which it may be perceptible to the eye.

For example, when the composition is applied to a skin whose luminance is, for example, less than or equal to 55, or to keratin fibers whose tone level is, for example, less than or equal to 6, the reflectance of the material treated with the combination of the at least one fluorescent compound and the at least one optical brightener is greater than that of a material treated with the at least one fluorescent compound alone, wherein the reflectance of an untreated material, in a range of from 550 nm to 700 nm, is less than that of materials treated on the one hand with the fluorescent compound and on the other hand with the combination of the fluorescent compound with the optical brightener.

In the case of a composition comprising only the optical brightener, the reflectance of a treated keratin material may be similar to that of an untreated material.

Moreover, the range within which the reflectance of the treated materials is greater than that of untreated materials can be broadened in the case of a composition comprising both the fluorescent compound and the optical brightener relative to that of a composition comprising only the fluorescent compound.

In addition, in the case of compositions applied to keratin fibers, such as the hair, the compounds employed herein may exhibit a high tinctorial affinity for these keratin fibers and good properties of resistance with respect to external agents.

Yet other characteristics and advantages of the present invention will appear more clearly on reading the description and examples which follow, and also FIGS. 1 and 2, attached. FIGS. 1 and 2 represent curves of reflectance as a function of wavelength for untreated chestnut brown hair, hair treated with a commercial product, hair treated with a composition comprising a fluorescent compound alone, and hair treated with a composition comprising the combination of a fluorescent compound and an optical brightener.

The keratin materials treated in accordance with the method disclosed herein are human in origin. In the text below, reference will be made to keratin materials in the knowledge that the keratin materials in question are human in origin.

Moreover, the keratin materials may be in the form of fibers or otherwise. Accordingly, the keratin materials may be the skin, hair, eyelashes, eyebrows, beard and moustache.

In one embodiment, the keratin material treated is the skin. For example, the skin has a luminance L* in the CIE L*a*b* system, measured using a Minolta CM 2002 calorimeter, of less than or equal to 55, wherein an L* value of zero is equivalent to black and of 100 to white.

The skin types corresponding to this luminance can be Asian skin, African skin, African-American skin, Spanish-American skin, Indian skin and Maghrebian skin.

In another embodiment, the keratin materials treated are in the form of fibers, such as pigmented keratin fibers and artificially colored fibers. For example, these fibers may be hair.

For example, the pigmented or artificially colored hair can have a tone level of less than equal to 6 (dark blond), such as less than or equal to 4 (chestnut brown).

The concept of "tone" is based on the classification of natural shades, with one tone separating each shade from that which immediately precedes it or follows it. This definition and the classification of natural shades are well known to hair professionals and published in the work "Sciences des traitements capillaires" by Charles ZVIAK 1988, Masson, pp. 215 and 278.

As described above, the method disclosed herein comprises applying to a keratin material a composition comprising, in a cosmetically acceptable medium, at least one fluorescent compound and at least one optical brightener for dyeing or coloring the keratin material with a lightening effect.

For greater clarity, the composition used in the method disclosed herein is detailed as follows.

The at least one fluorescent compound forming part of the composition used in the method disclosed herein is, for example, chosen from compounds which absorb light in the visible region of the spectrum, and possibly in the ultraviolet zone, and re-emit a fluorescent light in the visible spectrum whose wavelength is greater than that of the light absorbed. The wavelength of the light re-emitted can range from 500 nm to 700 nm.

In accordance with the method disclosed herein, the at least one fluorescent compound may be in a form which is soluble or insoluble in the medium of the composition at ambient temperature (ranging from 15 to 25° C.).

In one embodiment, the at least one fluorescent compound is chosen from compounds which are soluble in the medium of the composition.

For example, the at least one fluorescent compound is soluble in the medium of the composition at a level of at least 1 g/l, such as at least 5 g/l, at a temperature ranging from 15 to 25° C.

The at least one fluorescent compound which is soluble in the medium can be chosen, for example, from naphthalimides; 2H-1-benzopyran-2-ones (cationic or not) (coumarin compounds); xantheno-quinolizines such as sulforhodamines; aza-xanthenes; naphtholactams; azlactones; oxazines; thiazines; dioxazines; azoic, azomethine, and methine types of polycationic fluorescent dyes.

Among the fluorescent compounds soluble in the medium which can be used in the method disclosed herein, non-limiting mention may be made, for example, of the following:

Photosensitizing Dye NK-557, sold by UBICHEM, which has the following formula:

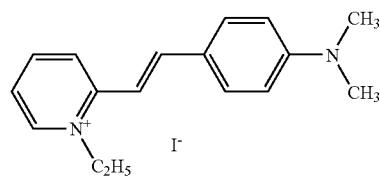

2-[2-(4-dimethylamino)phenylethenyl]-1-ethylpyridinium iodide;

Brilliant Yellow B6GL, sold by SANDOZ, of the following formula:

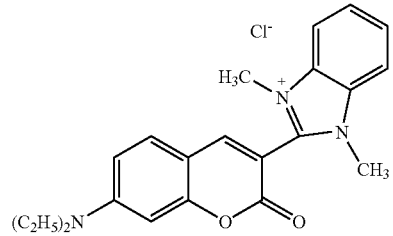

Basic Yellow 2, or Auramine O, sold by PROLABO, ALDRICH or CARLO ERBA, of the following formula:

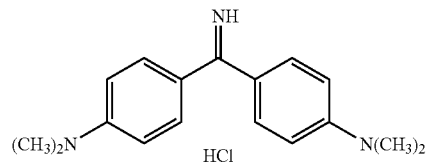

4,4'-(imidocarbonyl)bis(N,N-dimethylaniline) monohydrochloride; CAS No. 2465-27-2.

As far as the fluorescent compounds which are insoluble in the medium and can be used in the method disclosed herein are concerned, non-limiting mention may be made of, for example, inorganic fluorescent compounds such as those based on zinc oxide or zinc sulphide. Among organic fluorescent compounds insoluble in the medium, non-limiting mention may be made of, for example, pigments manufactured from fluorescent dyes, which are dissolved beforehand in a support resin in order to obtain a solid solution, which is subsequently milled to a powder of resin particles exhibiting fluorescent properties. The preparation of such fluorescent pigments is described, for example, in U.S. Pat. Nos. 2,851,424 and 3,856,550.

Insoluble fluorescent compounds may also be chosen from colored polyamide, formaldehyde/benzoguanamine, and melamine/formaldehyde/sulphonamide resins, from colored aminotriazine/formaldehyde/sulphonamide cocondensates from metallized polyester flakes, and from mixtures thereof. These fluorescent compounds may also be in the form of aqueous dispersions.

The at least one optical brightener forming part of the composition used in the method disclosed herein may be chosen from compounds which absorb light in the ultraviolet region of the spectrum, such as in the UVA, at a wavelength ranging from 300 nm to 390 nm. These compounds re-emit a fluorescent light in the visible spectrum, ranging from 400 nm to 525 nm.

Among optical brighteners, non-limiting mention may be made, for example, of stilbene derivatives, coumarin derivatives, oxazole and benzoxazole derivatives and imidazole derivatives.

Non-limiting mention may also be made, for example, of the following:
- the stilbene derivative of naphthotriazole (TINOPAL GS from Ciba), disodium 4,4'-distyrylbiphenylsulphonate (CTFA name: disodium distyrylbiphenyl disulphonate; TINOPAL CBS-X from Ciba, i.e., sodium 4,4'-bis[(4, 6-dianilino-1,3,5-triazin-2-yl)amino]stilbene-2,2'-disulphonate, the cationic derivative of aminocoumarin (TINOPAL SWN Conc. from Ciba), diethylaminomethylcoumarin, 4-methyl-7-diethylcoumarin, sodium 4,4'-bis[(4,6-dianilino-1,3,5-triazin-2-yl)amino]stilbene-2,2'-disulphonate (TINOPAL SOP from Ciba), 4,4'-bis[(4-anilino-6-bis(2-hydroxyethyl)amino-1,3,5-triazin-2-yl)amino]stilbene-2,2'-disulphonic acid (TINOPAL UNPA-GX from Ciba), 4,4'-bis[anilino-6-morpholine-1,3,5-triazin-2-yl)amino]stilbene (TINOPAL AMS-GX from Ciba) and disodium 4,4'-bis[(4-anilino-6-(2-hydroxyethyl)methylamino-1,3,5-triazin-2-yl) amino]stilbene-2,2'-sulphonate (TINOPAL 5BM-GX from Ciba),
- 2,5-thiophenediylbis(5-tert-butyl-1,3-benzoxazole) (UVITEX OB from Ciba),
- the anionic derivative of diaminostilbene (dispersion in water, LEUCOPHOR BSB liquid from Clariant), and optical brightener lakes (COVAZUR range from Wackherr).

The optical brighteners which can be used herein may also be present in the form of copolymers, for example, acrylates and/or methacrylates, grafted with optical brightener groups as described in application FR 99-10942.

In one embodiment, the at least one optical brightener is chosen such that the wavelength of the light re-emitted by the at least one optical brightener corresponds to the absorption wavelength of the at least one fluorescent compound present.

The at least one optical brightener used herein can be chosen, for example, from diethylaminomethylcoumarin, 4-methyl-7-diethylcoumarin, sodium 4,4'-bis[(4,6-dianilino-1,3,5-triazin-2-yl)amino]stilbene-2,2'-disulphonate, 2,5-thiophenediylbis(5-tert-butyl-1,3-benzoxazole) and disodium 4,4'-distyrylbiphenylsulphonate.

In one embodiment, the at least one optical brightener is chosen from compounds which are soluble in the medium of the composition at a level of at least 0.1 g/l, such as at least 0.5 g/l, at a temperature ranging from 15 to 25° C.

The minimum amounts of the at least one fluorescent compound and the at least one optical brightener in the composition are, for example, such that the reflectance of the treated material, measured in a range from 550 nm to 700 nm, is greater than the reflectance of the untreated keratin material.

For example, the at least one fluorescent compound is present in an amount ranging from 0.05 to 20% by weight relative to the total weight of the composition, such as from 0.05 to 10% by weight, further such as from 0.1 to 5% by weight relative to the total weight of the composition.

The at least one optical brightener is present in an amount ranging, for example, from 0.05 to 10% by weight, such as from 0.1 to 5% by weight relative to the total weight of the composition.

The cosmetically acceptable medium comprises water or a mixture of water and at least one organic solvent.

The at least one organic solvent can be chosen, for example, from linear and branched alkanols comprising from 1 to 4 carbon atoms, such as ethanol and isopropanol; polyols and polyol ethers such as glycerol, 2-butoxyethanol, propylene glycol, propylene glycol monomethyl ether, diethylene glycol monomethyl ether and monoethyl ether, and dimethoxyethane; aromatic alcohols such as benzyl alcohol and phenoxyethanol; ketones comprising from 3 to 4 carbon atoms; and $C_1$-$C_4$ alkyl acetates.

For example, the at least one organic solvent, if present, is present in an amount ranging from 1 to 40% by weight relative to the total weight of the composition, such as from 5 to 30% by weight relative to the total weight of the composition.

The pH of the composition used in the method disclosed herein ranges, for example, from 3 to 12, such as from 5 to 11.

The pH may be adjusted to the desired value using at least one agent chosen from commonly used acidifying and alkalifying agents.

Among the acidifying agents, mention may be made, for example, of mineral and organic acids such as hydrochloric acid, orthophosphoric acid, sulphuric acid, carboxylic acids such as acetic acid, tartaric acid, citric acid and lactic acid, and sulphonic acids.

Among the alkalifying agents, mention may be made, for example, of aqueous ammonia, alkali metal carbonates, alkanolamines such as mono-, di- and triethanolamines and their derivatives, sodium hydroxide and potassium hydroxide, and the compounds of formula (I):

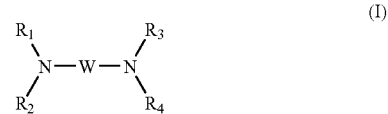

(I)

wherein W is a propylene residue optionally substituted by at least one entity chosen from a hydroxyl group and $C_1$-$C_6$ alkyl radicals, and $R_1$, $R_2$, $R_3$ and $R_4$, which may be identical or different, are each chosen from a hydrogen atom and $C_1$-$C_6$ alkyl radicals optionally carrying at least one hydroxyl radical.

In a first embodiment, the method disclosed herein comprises applying to keratin fibers, such as the hair, for coloring it while lightening it, a composition comprising, in a cosmetically acceptable medium, at least one fluorescent compound and at least one optical brightener. In this case, the composition comprises at least one fluorescent compound and at least one optical brightener, both of which are soluble in the medium of the composition.

The composition used in this embodiment of the method may further comprise, in addition to the at least one fluorescent compound and the at least one optical brightener, at least one additional direct dye.

For example, the at least one additional direct dye may be chosen from non-ionic, cationic and anionic direct dyes.

The at least one additional direct dye may, for example, be chosen from the following red and orange nitrobenzene dyes:
1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene, 1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitroparaphenylenediamine,
1-amino-2-nitro-4-(β-hydroxyethyl)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy)benzene,
1-(β,γ-dihydroxypropyl)oxy-3-nitro-4-(β-hydroxyethyl)aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine, and
1-amino-2-nitro-4-hydroxy-5-methylbenzene.

The composition used in this embodiment may comprise, in addition to or as replacement for these nitrobenzene dyes, at least one additional direct dye chosen from yellow, yellow-green, blue and violet nitrobenzene dyes, azo dyes, anthraquinone, naphthoquinone and benzoquinone dyes, indigoid dyes, and triarylmethane-derived dyes.

These additional direct dyes may, for example, be chosen from basic dyes, among which mention may be made, for example, of the dyes known in the Colour Index, 3rd edition, under the names Basic Brown 16, Basic Brown 17, Basic Yellow 57, Basic Red 76, Basic Violet 10, Basic Blue 26 and Basic Blue 99, acid direct dyes, among which mention may be made, for example, of the dyes known in the Colour Index, 3rd edition, under the names Acid Orange 7, Acid Orange 24, Acid Yellow 36, Acid Red 33, Acid Red 184, Acid Black 2, Acid Violet 43 and Acid Blue 62, and cationic direct dyes such as those described in documents WO 95/01772, WO 95/15144 and EP 714954.

Among the yellow and yellow-green nitrobenzene additional direct dyes mention may be made, for example, of compounds chosen from:
1-β-hydroxyethyloxy-3-methylamino-4-nitrobenzene,
1-methylamino-2-nitro-5-(β,γ-dihydroxypropyl)oxybenzene,
1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulphonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene, and
4-(β-hydroxyethyl)amino-3-nitrobenzamide.

Among blue and violet nitrobenzene additional direct dyes mention may be made, for example, of compounds chosen from:
1-(β-hydroxyethyl)amino-4-N,N-bis(β-hydroxyethyl)amino-2-nitrobenzene,
1-(γ-hydroxypropyl)amino-4-N,N-bis(β-hydroxyethyl)amino-2-nitrobenzene,
1-(β-hydroxyethyl)amino-4-(N-methyl-N-β-hydroxyethyl)amino-2-nitrobenzene,
1-(β-hydroxyethyl)amino-4-(N-ethyl-N-β-hydroxyethyl)amino-2-nitrobenzene,
1-(β,γ-dihydroxypropyl)amino-4-(N-ethyl-N-β-hydroxyethyl)amino-2-nitrobenzene, and
2-nitro-para-phenylenediamines of formula (II):

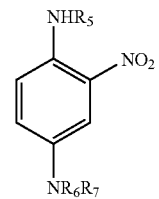

wherein:
$R_6$ is chosen from $C_1$-$C_4$ alkyl radicals and β-hydroxyethyl, β-hydroxypropyl and γ-hydroxypropyl radicals;
$R_5$ and $R_7$, which may be identical or different, are each chosen from β-hydroxyethyl, β-hydroxypropyl, γ-hydroxypropyl and β,γ-dihydroxypropyl radicals, wherein at least one of the radicals $R_6$, $R_7$ and $R_5$ is a γ-hydroxypropyl radical and it is not possible for $R_6$ and $R_7$ simultaneously to be a β-hydroxyethyl radical when $R_6$ is a γ-hydroxypropyl radical, such as those described in document FR 2 692 572.

When present, the at least one additional direct dye is present in an amount ranging, for example, from 0.0005 to 12% by weight relative to the total weight of the composition such as from 0.005 to 6% by weight relative to the total weight of the composition.

The composition may further comprise at least one oxidation base.

The at least one oxidation base may be chosen from the oxidation bases conventionally used for oxidation dyeing, such as para-phenylenediamines, bisphenylalkylenediamines, para-aminophenols, ortho-aminophenols and heterocyclic bases and their acid addition salts thereof and base addition salts thereof.

Among the para-phenylenediamines, mention may be made, for example, of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine and 4-aminophenyl- 1-(3-hydroxypropyl)pyrrolidine, and their acid addition salts thereof and base addition salts thereof.

Among the bisphenylalkylenediamines, mention may be made, for example, of N,N'-bis(β-hydroxyethyl)-N N'-bis (4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis (β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,5-dioxaoctane, and their acid addition salts thereof and base addition salts thereof.

Among the para-aminophenols, mention may be made, for example, of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and their acid addition salts thereof and base addition salts thereof.

Among the ortho-aminophenols, mention may be made, for example, of 2-aminophenol, 2-amino-5-methylphenol, 2-amino-6-methylphenol, 5-acetamido-2-aminophenol, and their acid addition salts thereof and base addition salts thereof.

Among the heterocyclic bases, mention may be made, for example, of pyridine derivatives, pyrimidine derivatives and pyrazole derivatives and their acid addition salts thereof and base addition salts thereof.

The at least one oxidation base, if present, is present in an amount ranging, for example, from 0.0005 to 12% by weight of the total weight of the composition such as from 0.0005 to 6% by weight relative to the total weight of the composition.

When it is intended for oxidation dyeing of keratin fibers, such as the hair, the composition may further comprise at least one coupler in order to modify or enrich with glints the shades obtained by using the at least one fluorescent compound, the at least one optical brightener and the at least one oxidation base.

The at least one coupler which can be used may be chosen from couplers used conventionally in this field, among which mention may be made, for example, of meta-phenylenediamines, meta-aminophenols, meta-diphenols and heterocyclic couplers and their acid addition salts thereof and base addition salts thereof.

The at least one coupler can, for example, be chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2,6-dimethylpyrazolo[1,5-b]-1, 2,4-triazole, 2,6-dimethyl[3,2-c]-1,2,4-triazole, 6-methylpyrazolo[1,5-a]benzimidazole, and their acid addition salts thereof and base addition salts thereof.

When present, the at least one coupler is present in an amount ranging, for example, from 0.0001 to 10% by weight relative to the total weight of the composition such as from 0.005 to 5% by weight relative to the total weight of the composition.

The acid addition salts that can be used in the context of the compositions disclosed herein for the at least one oxidation base and the at least one coupler are chosen, for example, from hydrochlorides, hydrobromides, sulphates, citrates, succinates, tartrates, tosylates, benzenesulphonates, lactates and acetates.

The base addition salts that can be used in the context of the composition disclosed herein for the at least one oxidation base and the at least one coupler are chosen, for example, from addition salts with at least one base agent chosen from alkali metals, alkaline-earth metals, aqueous ammonia, organic amines, including alkanolamines, and the compounds of formula (I).

When the composition according to the method disclosed herein is intended for coloring keratin fibers such as the hair, it may comprise at least one oxidizing agent chosen, for example, from hydrogen peroxide, urea peroxide, alkali metal bromides, persalts such as perborates and persulphates, and enzymes such as two-electron and four-electron oxidoreductases and peroxidases. In one embodiment, the at least one oxidizing agent chosen from hydrogen peroxide and enzymes is used.

If present, the at least one oxidizing agent is present in an amount ranging, for example, from 0.001 to 10% by weight relative to the total weight of the composition.

The composition used in the method disclosed herein may further comprise at least one adjuvant chosen from various adjuvants conventionally used in this type of composition, such as, for example, anionic, cationic and non-ionic surfactants and mixtures thereof, anionic, cationic, non-ionic, amphoteric and zwitterionic polymers and mixtures thereof, mineral and organic thickeners, antioxidants, penetrants, sequestrants, perfumes, buffers, dispersants, conditioning agents such as cations, cationic polymers and amphoteric polymers, modified and non-modified, volatile and non-volatile silicones, film formers, ceramides, preservatives, stabilizers and opacifiers.

Among the thickeners, mention may be made, for example, of thickening systems based on associative polymers, which are well known to the person skilled in the art and are, for example, non-ionic, anionic, cationic or amphoteric in nature.

It will be appreciated that the person skilled in the art will take care to select at least one optional complementary ingredient in a manner such that at least one of the advantageous properties intrinsically attached to the composition is not, or not substantially, adversely affected by the intended addition or additions.

The cosmetic composition for coloring keratin fibers, such as the hair, may be present in a variety of forms, such as lotions, shampoos, creams, gels, pastes and any other appropriate form.

In one embodiment, the composition according to the method disclosed herein is in the form of a coloring and lightening shampoo comprising, in a cosmetically acceptable aqueous medium, at least one fluorescent compound and at least one optical brightener as defined above, and at least one surfactant. The at least one fluorescent compound and the at least one optical brightener are, for example, soluble in the medium.

The at least one surfactant present in the shampoo may be chosen from anionic, cationic, amphoteric and non-ionic surfactants.

Among the non-ionic surfactants, mention may be made, for example, of alkylpolyglucosides.

In these shampoos, the at least one surfactant is present in an amount ranging, for example, from 4 to 30%, such as from 8 to 20%, by weight relative to the total weight of the shampoo composition.

In a second embodiment of the present disclosure, the method disclosed herein comprises applying a composition to keratin fibers, such as the hair, for producing on these keratin fibers a temporary or transient coloration with lightening effect that can be removed at the first shampooing or makeup removal. This composition comprises, in a cosmetically acceptable medium, at least one fluorescent compound and at least one optical brightener at least one of which, such as both, are insoluble in the medium of the composition.

In this embodiment, besides the at least one fluorescent compound and the at least one optical brightener, the composition may further comprise at least one non-fluorescent pigment.

The at least one non-fluorescent pigment is chosen, for example, from organic and mineral pigments which are cosmetically or dermatologically acceptable.

The at least one non-fluorescent pigment may be present in powder form or in the form of a pigment paste.

Reference may be made, for example, to document EP 808 150 in regard to the exemplary list of the pigments that can be used.

If present, the at least one non-fluorescent pigment is present, for example, in an amount such that it does not mask the fluorescence effect imparted by the at least one fluorescent compound and by the at least one optical brightener.

For example, the at least one non-fluorescent pigment, if present, is present in an amount ranging from 0.01 to 10% by weight relative to the total weight of the composition such as from 0.05 to 3% by weight relative to the total weight of the composition.

The pH of the compositions used in this embodiment ranges, for example, from 6 to 8 such as from 6 to 7.5.

Such compositions may further comprise at least one film-forming polymer which is in a form soluble or dispersed in the cosmetically acceptable medium of the composition.

In order to enhance, if necessary, at least one of the properties of the film formed, the composition may further comprise at least one plasticizer.

These compositions may further comprise at least one adjuvant chosen from various commonly used adjuvants, chosen, for example, from volatile and non-volatile, soluble and insoluble silicones; quaternized and non-quaternized proteins; sunscreen agents; surfactants; antifoams; moisturizers; humectants; emollients; vegetable and synthetic oils; preservatives and sequestrants; antioxidants; perfumes; alkalifying and acidifying agents; pigment suspension agents; and thickeners.

The compositions used in this embodiment may be present in at least one form chosen, for example, from liquids with a greater or lesser degree of thickening, creams and gels.

For example, the composition may be in the form of mascara for the eyelashes or hair mascara, to be applied, for example, by brush or by comb.

In a third embodiment, the method comprises applying to the skin, for dyeing and at the same time lightening the skin, a composition comprising, in a cosmetically acceptable medium, at least one fluorescent compound and at least one optical brightener. In this embodiment, the at least one fluorescent compound is insoluble in the medium for the composition.

In this embodiment, the composition comprises, for example, a fatty phase a fraction of which is not volatile (in other words, does not evaporate at a temperature ranging from 15 to 25° C.). This fatty phase may constitute the continuous phase or disperse phase of the composition.

The non-volatile fraction of the fatty phase may be chosen, for example, from non-volatile oils, waxes, gums, resins and paste-like fats of animal, vegetable, mineral or synthetic origin, and mixtures thereof.

For example, the non-volatile fraction of the fatty phase is present in an amount ranging, for example, from 1 to 85%, such as from 1% to 30%, by weight relative to the total weight of the composition.

In this embodiment, the compositions may further comprise at least one filler of the kind known as "soft-focus". The term "filler" means colorless or white, mineral or synthetic, lamellar or non-lamellar particles intended to endow the composition with body or rigidity and/or the makeup with softness, mattness and uniformity. Further, a soft-focus filler is a filler which additionally gives transparency to the complexion and a haze effect. This soft-focus effect is linked to the spectral reflectance of the filler.

The at least one filler may therefore be chosen, for example, from silica (for example SB-700 or SB-150 silica microbeads from Miyoshi), talc (for example P3 talc from Nippon Talc), silica/$TiO_2$ and silica/zinc oxide composites, polyethylene powder, starch powder, nylon powder (for example ORGASOL 2002 Extra D Nat Cos from Atochem), and styrene/acrylic copolymer powders.

For example, the at least one filler has an average particle size of less than or equal to 15 µm, such as less than or equal to 3 µm. In one example, the at least one filler is non-spherical.

Further for example, the at least one filler, if present, is present in an amount ranging from 0.1 to 20%, such as from 8% to 15%, by weight relative to the total weight of the composition.

In this embodiment, the composition may further comprise at least one additive chosen from additives conventional in the field, such as hydrophilic and lipophilic organic UV filters and mineral filters.

The at least one additive, if present, is present in an amount ranging, for example, from 0.1 to 20% by weight relative to the total weight of the composition.

Furthermore, this composition may comprise at least one moisturizing agent, chosen, for example, from urea and its derivatives, polyols, such as glycerol and sorbitol, and lipid vesicles, emulsified, for example, by at least one non-ionic surfactant in the composition, such as proteins, tocopherols, amino acids, allantoin, etc.

The pH of this type of composition ranges, for example, from 6.5 to 7.5.

In this embodiment, the composition may be in a form chosen from a cream, a gel and a milk. For example, the composition may be a foundation.

As indicated before, the compositions in the three embodiments, the nature of whose constituents, and their proportions, has been described above, and in any other embodiments disclosed herein, are intended for application to keratin materials.

In one embodiment, the composition is applied without rinsing and then the medium is evaporated or left to evaporate. This method can be used in the case where the keratin material is the skin or if the composition is intended for application to keratin fibers for the purpose of temporarily dyeing them.

In another embodiment, the method disclosed herein comprises:

applying the composition disclosed herein to a keratin material for a period sufficient to develop the desired coloration and lightening, rinsing the keratin material, optionally washing the keratin material with a cleansing composition and rinsing the keratin material, and drying the keratin material.

This method can be useful when the keratin materials treated are fibers such as the hair, moustache, beard and eyebrows.

For example, the cleansing composition can be a shampoo.

The time required for the development of the coloration and for the production of the lightening effect on the keratin fibers can range, for example, from 5 to 60 minutes such as from 5 to 40 minutes.

Moreover, the temperature for the development of the coloration and for the production of the lightening effect on the keratin fibers can range, for example, from the ambient temperature (15 to 25° C.) to 80° C., such as from 15 to 40° C.

In this embodiment, such as in the case of direct coloring or oxidation dyeing, the method disclosed herein comprises separately storing:

a first composition comprising, in a medium suitable for dyeing, at least one fluorescent compound and at least one optical brightener, and optionally at least one additional ingredient chosen from direct dyes, oxidation bases, and couplers, and a second composition comprising, in a medium suitable for dyeing, at least one oxidizing agent;

mixing the first composition and the second composition at the time of use, before applying this mixture to the keratin fibers for a time period sufficient to develop the desired colouring and lightening;

rinsing the keratin fibers;

optionally washing the keratin fibers with a cleansing composition and rinsing the keratin fibers; and drying the keratin fibers.

Further disclosed herein is a composition comprising, in a cosmetically acceptable medium, at least one fluorescent compound soluble in the medium and at least one optical brightener soluble in the medium.

For example, the at least one fluorescent compound is chosen from compounds soluble in the medium of the composition at a level of at least 1 g/l, such as at least 5 g/l, at a temperature ranging from 15 to 25° C.

The at least one optical brightener is, for example, chosen from compounds which are soluble in the medium of the composition at a level of at least 0.1 g/l, such as at least 0.5 g/l, at a temperature ranging from 15 to 25° C.

The lists of soluble fluorescent compounds and optical brighteners given above remain valid, and reference may be made thereto.

The amounts of the at least one fluorescent compound and the at least one optical brightener present in the composition, for example, are such that, following application to the keratin material whose tone level is not more than 6, such as not more than 4, the composition can give a reflectance, measured in a range from 550 nm to 700 nm, greater than the reflectance of the untreated keratin material.

For example, the at least one fluorescent compound is present in an amount ranging from 0.05 to 20% by weight relative to the total weight of the composition, such as from 0.05 to 10% by weight, further such as from 0.1 to 5% by weight relative to the total weight of the composition.

Furthermore, the at least one of optical brightener is present in an amount ranging, for example, from 0.05 to 10% by weight relative to the total weight of the composition, such as from 0.1 to 5% by weight relative to the total weight of the composition.

The cosmetically acceptable medium comprises water or a mixture of water and at least one organic solvent.

The at least one organic solvent may be chosen, for example, from linear and branched alkanols comprising from 1 to 4 carbon atoms; polyols and polyol ethers; and aromatic alcohols.

The at least one solvent, if present, is present in an amount ranging, for example, from 1 to 40% by weight relative to the total weight of the composition, such as from 5 to 30% by weight relative to the total weight of the composition.

The pH of the composition used herein ranges, for example, from 3 to 12 such as from 5 to 11.

The pH may be adjusted to the desired value using at least one agent chosen from acidifying and alkalifying agents which are commonly used, and of which lists have been indicated above.

The composition disclosed herein may further comprise at least one additional direct dye.

When present, the at least one additional direct dye is present in an amount ranging, for example, from 0.0005 to 12% by weight relative to the total weight of the composition such as from 0.005 to 6% by weight relative to the total weight of the composition.

The composition may likewise comprise at least one oxidation base.

If present, the at least one oxidation base is present in an amount ranging, for example, from 0.0005 to 12% by weight relative to the total weight of the composition such as from 0.005 to 6% by weight relative to the total weight of the composition.

Furthermore, the composition may comprise at least one coupler, so as to modify or enrich with glints the shades obtained using the at least one fluorescent compound, the at least one optical brightener and the at least one oxidation base.

When present, the at least one coupler is present in an amount ranging, for example, from 0.0001 to 10% by weight relative to the total weight of the composition such as from 0.005 to 5% by weight relative to the total weight of the composition.

In one embodiment, the composition comprises at least one oxidizing agent.

If present, the at least one oxidizing agent is present in an amount ranging, for example, from 0.001 to 10% by weight relative to the weight of the composition.

The composition used in the method disclosed herein may also comprise at least one adjuvant chosen from various adjuvants conventionally used in this type of composition.

As to the nature of the direct dyes, oxidation bases, couplers and other adjuvants of the composition, reference may be made to the lists given in the context of the description of the compositions used in the method disclosed herein.

The cosmetic composition for coloring keratin fibers may be present in a form chosen from, for example, lotions, shampoos, creams, gels, pastes and any other appropriate form.

In one embodiment, the composition is in the form of a coloring and lightening shampoo comprising, in a cosmetically acceptable aqueous medium, at least one fluorescent compound and at least one optical brightener, as defined above, and at least one surfactant.

The at least one surfactant present in the shampoo may be chosen from anionic, cationic, amphoteric and non-ionic surfactants.

Among the non-ionic surfactants, mention may be made, for example, of alkylpolyglucosides.

In these shampoos, the at least one surfactant is present in a an amount ranging from 4 to 30% such as from 8 to 20% by weight relative to the total weight of the shampoo composition.

Further disclosed herein is a device comprising at least two compartments, wherein at least one compartment comprises a composition comprising, in a cosmetically acceptable medium, at least one fluorescent compound and at least one optical brightener and optionally at least one additional ingredient chosen from direct dyes, oxidation bases and couplers, and at least one other compartment comprises a composition comprising at least one oxidizing agent.

In one embodiment, the composition comprises at least one fluorescent compound and at least one optical brightener both of which are soluble in the medium, as described above.

The device comprising at least two compartments may be equipped with an implement allowing the desired mixture to be delivered to the hair, such as the devices described in document FR 2 586 913.

Examples which do not, however, limit the disclosure are as follows.

EXAMPLES

The following three direct dyeing compositions were prepared (amounts expressed in grams):

| Compositions | 1 comparative | 2 invention | 3 invention |
|---|---|---|---|
| Fluorescent dye (a) | 0.5 | 0.5 | 0.5 |
| Optical brightener: diethylaminomethylcoumarin | — | 0.5 | — |
| Optical brightener: 4-methyl-7-diethylcoumarin | — | — | 0.5 |
| Hydroxyethylcellulose | 1.6 | 1.6 | 1.6 |
| Alkyl (C8/C10 - 50/50) polyglucoside at 60% in buffered aqueous solution | 6 AS* | 6 AS* | 6 AS* |
| Benzyl alcohol | 8 | 8 | 8 |
| Polyethylene glycol | 12 | 12 | 12 |
| Mixture of methyl, butyl, ethyl, propyl and isobutyl p-hydroxybenzoates | 0.12 | 0.12 | 0.12 |
| Demineralized water qs | 100 | 100 | 100 |

AS* denotes active substance (a) the fluorescent dye is Photosensitizing Dye NK-557, sold by Ubichem.

The tests were conducted on locks of chestnut brown hair with a tone level of 4.

The composition was applied to chestnut brown hair at 10 grams of composition per gram of hair. The composition was spread out first to cover all of the hair. The composition was left to act for 20 minutes at ambient temperature (from 20 to 25° C.). The hair was subsequently rinsed with water, then washed with a shampoo based on lauryl ether sulphate. It was subsequently dried.

The lightening performance of the compositions in accordance with the invention, expressed as a function of the reflectance of the hair, was compared with the reflectance of a lock of untreated hair and to that obtained with the commercial lightening product "Lumiblonde" (chemical bleaching).

The reflectance was measured by means of a spectrophotocolorimeter apparatus and following irradiation of the hair with visible light in the wavelength ranging from 400 to 700 nm.

Figure 1:
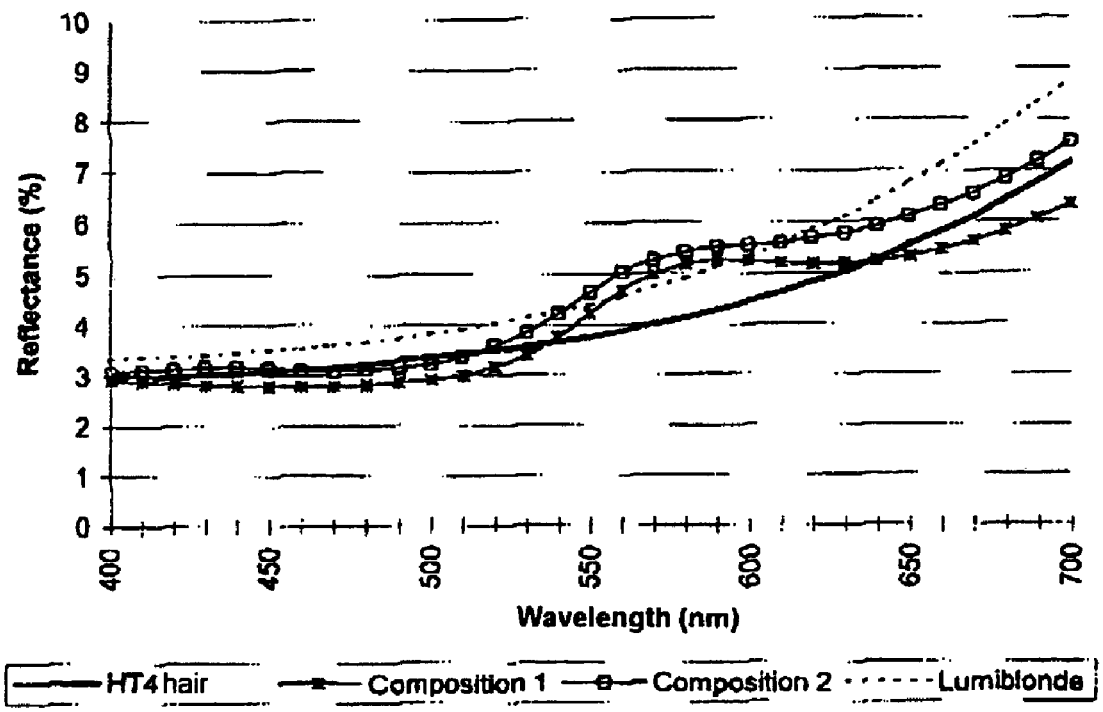
FIG. 1 represents the reflectance as a function of wavelength of untreated chestnut brown hair, of hair treated with the commercial product "Lumiblonde", of hair treated with composition 1 (fluorescent compound alone) and of hair treated with composition 2 (fluorescent compound and optical brightener).
Figure 2:
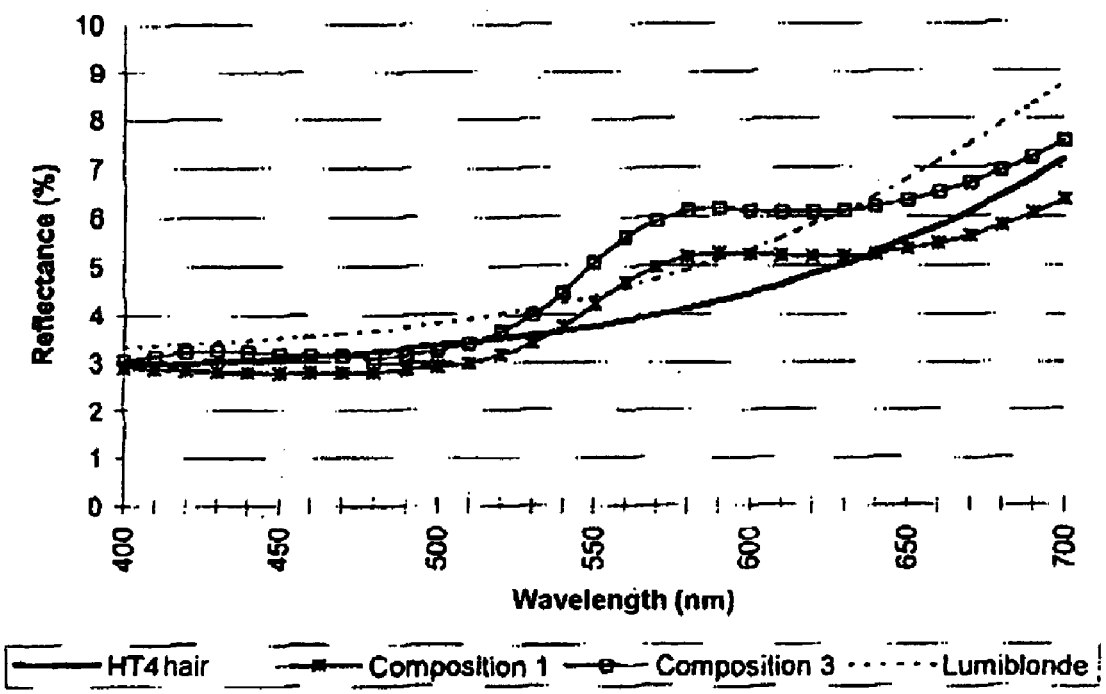
FIG. 2 represents the reflectance as a function of wavelength of untreated chestnut brown hair, of hair treated with the commercial product "Lumiblonde", of hair treated with composition 1 (fluorescent compound alone) and of hair treated with composition 3 (fluorescent compound and optical brightener).

It was first observed that the reflectance of a lock of hair treated with a composition according to the invention is greater than that of untreated hair. The treated locks therefore appeared lighter.

It was notable that the reflectance of a lock of hair treated with a composition comprising 0.5 g of an optical brightener is similar to that of a lock of untreated hair. No lightening effect was observed in this case.

Moreover, the combination of the fluorescent compound and the optical brightener gave higher percentage reflectances than those obtained with the fluorescent compound alone, and did so over a wavelength range which is broader than that obtained with the fluorescent compound alone.

Accordingly, the composition comprising a combination of the at least one fluorescent compound and the at least one optical brightener can also make it possible to obtain a more marked, more natural and aesthetic lightening effect than that obtained with the fluorescent compound alone.

What is claimed is:

1. A method of dyeing or coloring, with a lightening effect, a human keratin material, having a tone level of less than or equal to 6, comprising applying to said human keratin material a composition comprising, in a cosmetically acceptable medium, at least one fluorescent compound soluble in the medium and at least one optical brightener;
   wherein the at least one fluorescent compound and the at least one optical brightener are present in the composition in a combined amount effective to provide a lightening effect on keratin materials that have a tone level of less than or equal to 6.

2. The method according to claim 1, wherein the composition is applied to the keratin material without rinsing and said medium is then evaporated or left to evaporate.

3. The method according to claim 1, comprising:
   applying the composition to the keratin material for a time period sufficient to develop the desired coloration and lightening,
   rinsing the keratin material,
   optionally washing the keratin material with a cleansing composition and then rinsing the keratin material, and
   drying the keratin material.

4. The method according to claim 1, wherein the at least one fluorescent compound absorbs light in the visible region of the spectrum, and optionally in the ultraviolet zone, and re-emits in the visible spectrum a fluorescent light having a greater wavelength than the light absorbed, said wavelength ranging from 500 to 700 nm.

5. The method according to claim 1, wherein the at least one optical brightener absorbs light in the ultraviolet region of the spectrum and re-emits a fluorescent light in the visible spectrum, ranging from 400 to less than 525 nm.

6. The method according to claim 1, wherein the amount of the at least one fluorescent compound and the amount of the at least one optical brightener are such that, following application to the keratin material, the composition gives a reflectance, measured in a range from 550 nm to 700 nm, which is greater than the reflectance of the untreated said keratin material.

7. The method according to claim 1, wherein the at least one fluorescent compound is present in an amount ranging from 0.05 to 20% by weight relative to the total weight of the composition.

8. The method according to claim 7, wherein the at least one fluorescent compound is present in an amount ranging from 0.05 to 10% by weight relative to total weight of the composition.

9. The method according to claim 8, wherein the at least one fluorescent compound is present in an amount ranging from 0.1 to 5% by weight relative to the total weight of the composition.

10. The method according to claim 1, wherein the at least one optical brightener is present in an amount ranging from 0.05 to 10% by weight relative to the total weight of the composition.

11. The method according to claim 10, wherein the at least one optical brightener is present in an amount ranging from 0.1 to 5% by weight relative to the total weight of the composition.

12. The method according to claim 1, wherein the cosmetically acceptable medium comprises water and optionally at least one organic solvent.

13. The method according to claim 1, wherein the pH of the composition ranges from 3 to 12.

14. The method according to claim 13, wherein the pH of the composition ranges from 5 to 11.

15. The method according to claim 1, wherein the composition further comprises at least one additional direct dye chosen from non-ionic, cationic and anionic direct dyes.

16. The method according to claim 15, wherein the at least one additional direct dye is chosen from nitrobenzene dyes.

17. The method according to claim 15, wherein the at least one additional direct dye is chosen from azo dyes, anthraquinone, naphthoquinone and benzoquinone dyes, indigoid dyes and triarylmethane-derived dyes.

18. The method according to claim 15, wherein the at least one additional direct dye is present in an amount ranging from 0.0005 to 12% by weight relative to the total weight of the composition.

19. The method according to claim 18, wherein the at least one additional direct dye is present in an amount ranging from 0.005 to 6% by weight relative to the total weight of the composition.

20. The method according to claim 1, wherein the composition comprises at least one oxidation base chosen from para-phenylenediamines, bisphenylalkylenediamines, para-aminophenols, ortho-aminophenols and heterocyclic bases, and acid addition salts thereof, and base addition salts thereof.

21. The method according to claim 20, wherein the at least one oxidation base is present in an amount ranging from 0.0005 to 12% by weight relative to the total weight of the composition.

22. The method according to claim 21, wherein the at least one oxidation base is present in an amount ranging from 0.005 to 6% by weight relative to the total weight of the composition.

23. The method according to claim 20, wherein the composition comprises at least one coupler chosen from meta-phenylenediamines, meta-aminophenols, meta-diphenols and heterocyclic couplers, and acid addition salts thereof, and base addition salts thereof.

24. The method according to claim 23, wherein the at least one coupler is present in an amount ranging from 0.0001 to 10% by weight relative to the total weight of the composition.

25. The method according to claim 24, wherein the at least one coupler is present in an amount ranging from 0.005 to 5% by weight relative to the total weight of the composition.

26. The method according claim 1, wherein the composition further comprises at least one oxidizing agent.

27. The method according to claim 26, wherein the at least one oxidizing agent is chosen from hydrogen peroxide, urea peroxide, alkali metal bromides, persalts, and enzymes.

28. The method according to claim 27, wherein the persalts are chosen from perborates and persulphates.

29. The method according to claim 27, wherein the enzymes are chosen from two-electron and four-electron oxidoreductases and peroxidases.

30. The method according to claim 1, wherein the composition further comprises at least one surfactant chosen from anionic, cationic, amphoteric and non-ionic surfactants.

31. The method according to claim 1, comprising:
separately storing
a first composition comprising, in a medium suitable for dyeing, at least one fluorescent compound and at least one optical brightener, and optionally at least one additional ingredient chosen from direct dyes, oxidation bases, and couplers, and
a second composition comprising, in a medium suitable for dyeing, at least one oxidizing agent;
mixing the first composition and the second composition at the time of use;
applying this mixture to the keratin material for a time period sufficient to develop the desired coloration;
rinsing the keratin material;
optionally washing the keratin material with a cleansing composition and rinsing the keratin material; and
drying the keratin material.

32. The method according to claim 31, wherein the keratin material is hair.

33. The method according to claim 1, wherein the composition is in the form of a coloring shampoo.

34. The method according to claim 1, wherein the composition further comprises at least one non-fluorescent pigment.

35. The method according to claim 34, wherein the at least one non-fluorescent pigment is present in an amount ranging from 0.01 to 10% by weight relative to the total weight of the composition.

36. The method according to claim 35, wherein the at least one non-fluorescent pigment is present in an amount ranging from 0.05 to 3% by weight relative to the total weight of the composition.

37. The method according to claim 34, wherein the pH of the composition ranges from 6 to 8.

38. The method according to claim 34, wherein the composition is in a form chosen from a mascara for eyelashes and a hair mascara.

39. The method according to claim 1, wherein the keratin material is chosen from skin and keratin fibers.

40. The method according to claim 39, wherein the skin exhibits a luminance L in the CIEL*a*b* system of less than or equal to 55.

41. The method according to claim 39, wherein the keratin material is chosen from keratin fibers.

42. The method according to claim 1, wherein the keratin fibers exhibit a tone level of less than or equal to 4.

43. The method according to claim 1, wherein the at least one fluorescent compound soluble in the medium is chosen from naphthalimides; 2H-1-benzopyran-2-ones; xanthenoquinolizines; aza-xanthenes; naphtholactams; azlactones; oxazines; thiazines; dioxazines; azoic, azomethine, and methine types of polycationic fluorescent dyes.

44. The method according to claim 1, wherein the at least one fluorescent compound soluble in the medium is chosen from compounds of the following formulae:

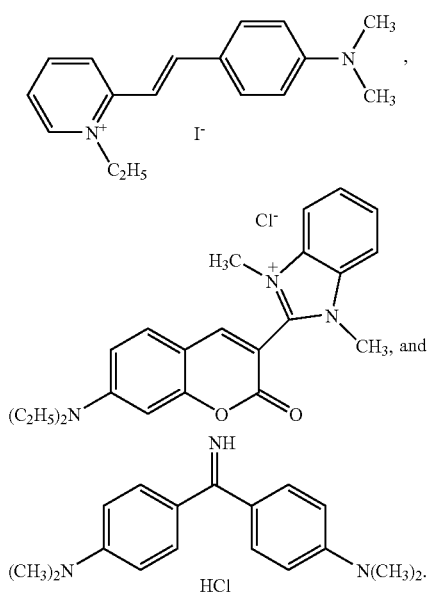

45. The method according to claim 1, wherein the at least one optical brightener is chosen from stilbene derivatives, coumarin derivatives, oxazole and benzoxazole derivatives and imidazole derivatives.

46. The method according to claim 1, wherein the at least one optical brightener is chosen such that the wavelength of the light re-emitted by the at least one optical brightener corresponds to the absorption wavelength of the at least one fluorescent compound present.

47. The method according to claim 1, wherein the at least one optical brightener is chosen from diethylaminomethylcoumarin, 4-methy-7-diethylcoumarin, sodium 4,4'-bis[(4,6-dianilino-1,3,5-triazin-2-yl)amino]stilbene-2,2'-disulphonate, 2,5-thiophenediylbis(5-tert-butyl-1,3-benzoxazole) and disodium 4,4'-distyrylbiphenyl-sulphonate.

48. A composition for dyeing keratin material having a tone level of less tha or equal to 6 with lightening effect comprising, in a cosmetically acceptable medium, at least one fluorescent compound soluble in the medium and at least one optical brightener soluble in the medium;
  wherein the at least one fluorescent compound and the at least one optical brightener are present in the composition in a combined amount effective to provide a lightening effect on keratin materials having a tone level of less than or equal to 6.

49. The composition according to claim 48, wherein the at least one fluorescent compound absorbs light in the visible region of the spectrum, and optionally in the ultraviolet zone, and re-emits in the visible spectrum a fluorescent light having a greater wavelength than the light absorbed, said wavelength ranging from 500 to 700 nm.

50. The composition according to claim 48, wherein the at least one fluorescent compound is present in an amount ranging from 0.05 to 20% by weight relative to the total weight of the composition.

51. The composition according to claim 50, wherein the at least one fluorescent compound is present in an amount ranging from 0.05 to 10% by weight relative to the total weight of the composition.

52. The composition according to claim 51, wherein the at least one fluorescent compound is present in an amount ranging from 0.1 to 5% by weight relative to the total weight of the composition.

53. The composition according to claim 48, wherein the at least one optical brightener absorbs light in the ultraviolet region of the spectrum and re-emits in the visible spectrum a fluorescent light having a wavelength ranging from 400 nm to 525 nm.

54. The composition according to claim 48, wherein the at least one optical brightener is present in an amount ranging from 0.05 to 10% by weight relative to the total weight of the composition.

55. The composition according to claim 54, wherein the at least one optical brightener is present in an amount ranging from 0.1 to 5% by weight relative to the total weight of the composition.

56. The composition according to claim 48, wherein the cosmetically acceptable medium comprises water and optionally at least one organic solvent.

57. The composition according to claim 48, wherein the pH of the composition ranges from 3 to 12.

58. The composition according to claim 57, wherein the pH of the composition ranges from 5 to 11.

59. The composition according to claim 48, wherein the composition comprises at least one additional direct dye chosen from non-ionic, cationic and anionic direct dyes.

60. The composition according to claim 59, wherein the at least one additional direct dye is chosen from nitrobenzene dyes.

61. The composition according to claim 59, wherein the at least one additional direct dye is chosen from azo dyes, anthraquinone, naphthoquinone and benzoquinone dyes, indigoid dyes and triarylmethane-derived dyes.

62. The composition according to claim 59, wherein the at least one additional direct dye is present in an amount ranging from 0.0005 to 12% by weight relative to the total weight of the composition.

63. The composition according to claim 62, wherein the at least one additional direct dye is present in an amount ranging from 0.005 to 6% by weight relative to the total weight of the composition.

64. The composition according to claim 48, wherein the composition comprises at least one oxidation base chosen from para-phenylenediamines, bisphenylalkylenediamines, para-aminophenols, ortho-aminophenols and heterocyclic bases and acid addition salts thereof and base addition salts thereof.

65. The composition according to claim 64, wherein the at least one oxidation base is present in an amount ranging from 0.0005 to 12% by weight relative to the total weight of the composition.

66. The composition according to claim 65, wherein the at least one oxidation base is present in an amount ranging from 0.005 to 6% by weight relative to the total weight of the composition.

67. The composition according to claim 64, wherein the composition further comprises at least one coupler chosen from meta-phenylenediamines, meta-aminophenols, meta-diphenols and heterocyclic couplers and acid addition salts thereof and base addition salts thereof.

68. The composition according to claim 67, wherein the at least one coupler is present in an amount ranging from 0.0001 to 10% by weight relative to the total weight of the composition.

69. The composition according to claim 68, wherein the at least one coupler is present in an amount ranging from 0.005 to 5% by weight relative to the total weight of the composition.

70. The composition according to claim 48, wherein the composition further comprises at least one oxidizing agent.

71. The composition according to claim 70, wherein the at least one oxidizing agent is chosen from hydrogen peroxide, urea peroxide, alkali metal bromides, persalts, and enzymes.

72. The composition according to claim 71, wherein the persalts are chosen from perborates and persulphates.

73. The composition according to claim 71, wherein the enzymes are chosen from two-electron and four-electron oxidoreductases and peroxidases.

74. The composition according to claim 48, wherein the composition further comprises at least one surfactant chosen from anionic, amphoteric, cationic and non-ionic surfactants.

75. The composition according to claim 48, wherein the composition is in a form chosen from a cream, a paste and a gel.

76. The composition according to claim 48, wherein the composition is in a form of a coloring shampoo.

77. The composition according to claim 48, wherein the at least one fluorescent compound soluble in the medium is chosen from naphthalimides; 2H-1-benzopyran-2-ones; xantheno-quinolizines; aza-xanthenes; naphtholactams; azlactones; oxazines; thiazines; dioxazines; azoic, azomethine, and methine types of polycationic fluorescent dyes.

78. The composition according to claim 48, wherein the at least one fluorescent compound soluble in the medium is chosen from compounds of the following formulae:

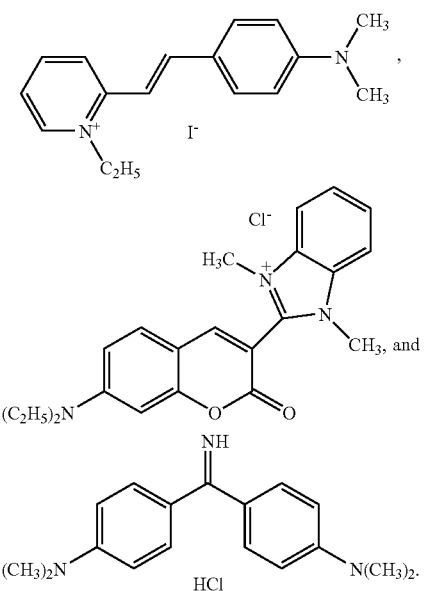

79. A device comprising at least two compartments, wherein at least one compartment comprises, in a cosmetically acceptable medium, a first composition for dyeing keratin material having a tone level of less than or equal to 6 with a lightening effect comprising at least one fluorescent compound soluble in the medium and at least one optical brightener and optionally at least one additional ingredient chosen from direct dyes, oxidation bases and couplers, and at least one other compartment comprises a second composition comprising at least one oxidizing agent;
  wherein the at least one fluorescent compound and the at least one optical brightener are present in the first composition in a combined amount effective to provide a lightening effect on keratin materials having a tone level of less than or equal to 6.

80. The device according to claim 79, wherein the at least one optical brightener is soluble in the medium.

* * * * *